United States Patent
Killion et al.

(10) Patent No.: US 8,249,285 B2
(45) Date of Patent: Aug. 21, 2012

(54) METHOD AND APPARATUS FOR PRODUCING NON LINEAR SOUND ATTENUATION

(75) Inventors: Mead Killion, Elk Grove Village, IL (US); Ron Scicluna, Hampshire, IL (US)

(73) Assignee: Etymotic Research Inc., Elk Grove Village, IL (US)

( * ) Notice: Subject to any disclaimer, the term of this patent is extended or adjusted under 35 U.S.C. 154(b) by 680 days.

(21) Appl. No.: 12/492,774

(22) Filed: Jun. 26, 2009

(65) Prior Publication Data

US 2010/0329475 A1  Dec. 30, 2010

(51) Int. Cl.
*H04R 25/00* (2006.01)
(52) U.S. Cl. ......................... 381/372; 381/370
(58) Field of Classification Search .................. 381/23.1, 381/71.7, 72, 370, 372, 380; 128/864, 867; 2/209; 181/129, 130, 135, 175, 198, 199, 181/224, 286
See application file for complete search history.

(56) References Cited

U.S. PATENT DOCUMENTS

| | | | |
|---|---|---|---|
| 4,807,612 A * | 2/1989 | Carlson | 381/380 |
| 4,852,683 A | 8/1989 | Killion | |
| 4,924,502 A | 5/1990 | Allen et al. | |
| 5,113,967 A | 5/1992 | Killion et al. | |
| 5,203,352 A | 4/1993 | Gardner, Jr. | |
| 5,936,208 A | 8/1999 | Hamery | |
| 6,068,079 A * | 5/2000 | Hamery et al. | 181/129 |

OTHER PUBLICATIONS

M. Killion et al., "An Earplug with Uniform 15-dB Attenuation," The Hearing Journal, vol. 41 (5); pp. 14-17 (1988).
M. Altshuler, "Balanced Attenuation Ear Protection," Sound & Communications, vol. 35, No. 3; pp. 12-14 (1989).

* cited by examiner

*Primary Examiner* — Brian Ensey
(74) *Attorney, Agent, or Firm* — McAndrews, Held & Malloy, Ltd.

(57) ABSTRACT

Certain embodiments of the present technology provide a sound attenuator for reducing high level sounds within the ear canal while maintaining high audibility for lower level sounds. The sound attenuator comprises a housing with a passageway for passing external sound, a damping member to restore resonance within a plugged ear, and a disc interposed across the passageway. The disc comprises a cavity, at least one hole through said disc and a flexible diaphragm positioned across the cavity. At a sound pressure level less than that of a predetermined value the flexible diaphragm expands upon an increase in the external sound pressure level maintaining a near constant level of attenuation. For sound pressure levels at or greater than that of the predetermined value the diaphragm contacts the interior surface of the cavity, thereby limiting the flexibility of the diaphragm and increasing the level of attenuation provided by the attenuator.

21 Claims, 18 Drawing Sheets

METHOD AND APPARATUS FOR PRODUCING NON LINEAR SOUND ATTENUATION

FIELD OF THE INVENTION

Certain embodiments of the present invention relate to methods for reducing the noise within an ear canal. More specifically, certain embodiments of the present invention relate to methods and apparatuses for providing non linear noise attenuation such that the attenuation is higher for high level external sounds than for lower level external sounds.

BACKGROUND OF THE INVENTION

It is highly documented that military personnel exposed to blasts from firearms, explosions and other high level peak noises are at high risk for hearing loss. Sound pressure levels (SPLs) over 160 dB that occur over periods as short as even a few milliseconds are sufficient to cause damage to the unprotected ear. Exposure to the peak noises caused by gunfire or other explosions adds hearing loss to the long list of risks and dangers encountered by soldiers on the battle field. One means to prevent hearing loss is to wear a noise attenuating device such as ear plugs or earmuffs. U.S. Pat. No. 5,203,352 issued to Gardner presents high-attenuation foam earplugs which may provide up to 40 dB of attenuation when properly inserted. Accordingly, the Gardner earplugs will reduce hazardous external peak SPLs of 160 to 190 dB to safer levels of 120 to 150 dB, respectively, within the ear canal of the wearer.

The Gardner and other similar earplugs will attenuate up to 40 dB of noise, but the attenuation level is independent of the level external sound. In other words, all external noises will be attenuated the same amount whether the sounds are extremely loud or very soft. Thus, softer sounds that would otherwise be audible without the use of earplugs may become inaudible or become so soft that they go unnoticed. For many work environments the perception of soft sounds is vital to the task at hand or the safety of the workers. For example, a soldier wearing earplugs as described attenuating a constant 40 dB of noise may fail to hear an enemy quietly approaching or fail to perceive communications from fellow soldiers. Likewise, a construction worker wearing such earplugs may receive adequate protection from high level construction sounds, but fail to hear a distant coworker's emergency call for help.

Many earplugs, like those described by Gardner, for example, may distort the reception of normal sound. The earplugs attenuate higher frequency sounds at a higher level than lower frequency sounds making it difficult for the wearer to hear or understand speech and other important sounds. High-audibility earplugs such as those described by U.S. Pat. No. 4,807,612 issued to Carlson, U.S. Pat. No. 5,113,967 issued to Killion et al., and U.S. Pat. No. 4,852,683 issued to Killion and products such as the ER-15® and ER-20® series earplugs produced by Etymotic Research, Inc.® produce relatively uniform attenuation across audible frequency ranges and a low enough attenuation such that speech and music remain highly audible to the wearer. While the high audibility of these earplugs allows the wearer to hear softer noises, they may not provide adequate protection for extremely high level sounds. A soldier wearing these ear plugs may still be able to hear a quietly approaching enemy, but the soldier's ears will remain exposed to dangerous noise levels that occur during battle.

An improved earplug with sound level dependent attenuation is described in U.S. Pat. No. 4,924,502 issued to Allen, et al. and U.S. Pat. No. 5,936,208 issued to Hamery and is embodied in a product sold by AEARO Technologies under the trade name Combat Arms Earplug. The Combat Arms Earplug introduces less noise attenuation for external SPLs below 110 dB than for external SPLs above 110 dB, but does not provide a constant attenuation across all frequencies. For example, where the external SPLs is below 110 dB the Combat Arms Earplug provides around 5 dB of attenuation at low frequencies and up to 20 dB attenuation at higher frequencies. Where the external SPL is above 110 dB, the attenuation provided increases by approximately 0.5 dB for each 1 dB increase of external sound until a maximum level of attenuation is achieved. The Combat Arms Earplug provides a passageway that allows partially unobstructed travel of sound from the exterior into the ear canal with a low level of attenuation at low sound pressure levels. A sharp obstruction located within the passageway of the Combat Arms Earplug causes the flow of sound within the earplug to become turbulent above 110 dB. This introduction of turbulent flow impedes the flow of the sound into the ear, thereby establishing greater attenuation. While the aforementioned earplugs may provide non linear pattern attenuation, they do not provide the high levels of sound attenuation necessary to adequately protect against high-level noises. Nor do they provide a constant attenuation level across all frequencies.

Thus, there exists a need for non linear attenuation earplug that provides a low, uniform attenuation at all frequencies and SPLs for external SPLs below a certain value (e.g. 110 dB SPL), yet provides a higher and increasing level of attenuation for external SPLs above that certain value.

Further limitations and disadvantages of conventional and traditional approaches will become apparent to one of skill in the art through comparison of such systems with some aspects of the present invention as set forth in the remainder of the present application.

BRIEF SUMMARY OF THE INVENTION

Certain embodiments of the present technology provide a device for attenuating sound within the ear canal where the amount of sound attenuated is greater for higher external sound levels than for lower sound levels. Certain embodiments of the present technology provide an ear protector for insertion into the ear that attenuates high level noises to a lower level in the ear canal while providing for high audibility during normal sound environments. Certain embodiments of the present technology provide an ear protector that produces a relatively constant level of attenuation across all audible external sound frequencies.

Certain embodiments of the present technology provide an ear protecting device to reduce high level sounds while maintaining high audibility of low level sounds within the ear canal. For example, an earmold provides a seal of the ear canal into which an ear protector (or ear protector) may be inserted. Provided within the ear protector are a damping member and a perforated disc. The disc contains a cavity and a flexible diaphragm situated within the cavity. The damping member preserves the frequency characteristic (or resonance) that the eardrum normally experiences. Thus, the sound delivered to the eardrum is substantially that which would have been observed at the eardrum in the absence of the ear protecting device, but it is decreased by an attenuation factor. The diaphragm within the disc flexes with an increase in sound pressure and attenuates external sound at a constant and relatively lower amount. At a predetermined external sound level the sound pressure causes the diaphragm to flex to a point where the diaphragm contacts the interior surface of the cavity of the disc. At this external sound level, and for external sounds greater than this level, the flexibility of the diaphragm is restricted by the presence of the interior wall of the disc. The flexibility of the diaphragm is thereby limited to its contact location at the holes in the plate. The reduction in flexibility correspondingly decreases the acoustical compliance of the ear protector. As a result of the decreased compliance the ear protector provides greater sound attenuation.

Certain embodiments of the present technology provide a non-linear sound attenuator and a method for using the same to reduce noise within the ear canal. The non-linear sound attenuator comprises a housing with a hollow passageway for passing external sound through the insert into the plug. The housing comprises a damping member situated within the housing and an attenuating disc interposed across the hollow passageway. The attenuating disc comprises a cavity with an interior surface and at least one hole through the disc. A flexible diaphragm is positioned across the cavity. At a sound pressure level less than that of a predetermined value the flexible diaphragm expands upon an increase in the external sound pressure level. Sound pressure causes the flexible diaphragm to expand. At a sound pressure level at or greater than that of the predetermined value the flexible diaphragm contacts said interior surface of said cavity, thereby limiting the flexibility of the diaphragm. In certain embodiments, for example, the attenuator provides a higher level of sound attenuation where the external sound pressure is above the predetermined value than for external sound pressure levels below the predetermined value. In other embodiments of the present technology, the non-linear sound attenuator may be inserted into an earmold or an ear plug to form a seal when inserted into the ear canal.

Certain embodiments of the present technology have characteristics for allowing sound to enter the ear canal with little to no attenuation at lower decibel levels. Additionally, certain embodiments of the present technology have characteristics of attenuating louder sounds to a greater extent than lower level sounds.

Various advantages, aspects and novel features of the present invention, as well as details of illustrated embodiments thereof, will be more fully understood from the following description and drawings.

DESCRIPTION OF A PREFERRED EMBODIMENT

Figure 1:
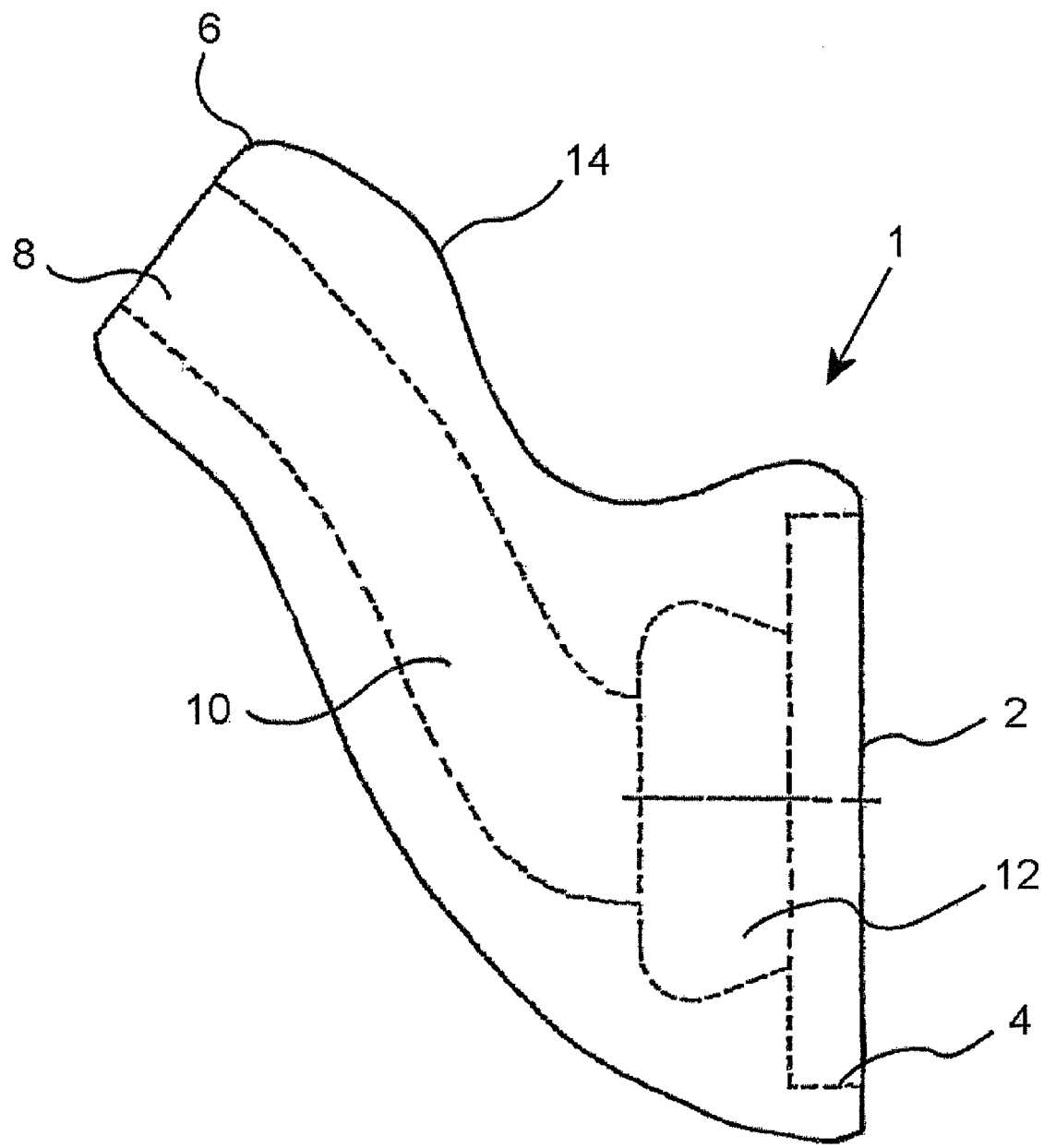
FIG. 1 depicts a side view of an earmold used in accordance with an embodiment of the present technology.

While the present invention is susceptible of embodiment in many different forms, there is shown in the drawings and will herein be described in detail certain preferred embodiments. It should be understood that the present disclosure is to be considered as an exemplification of the principles of the present technology, and is not intended to limit the broad aspect of the invention to the embodiments illustrated.

In the Figures, like elements are identified by numerals. FIG. 1 depicts an earmold 1 for insertion into the ear canal. The present invention is not meant to be limited by the size, shape or structure of the earmold 1. The invention is intended to be used with any earmold that is adapted to receive the ear protector 100 and form an adequate seal when inserted into the ear canal. However, the shape, material and structure of the ear protector 100 itself may be insertable into an ear, making the earmold unnecessary. A variety of different earmolds 1 are provided by companies such as All American Mold Laboratories, Inc. (see http://www.allamericanmold.com), or Westone (see www.westone.com). FIG. 1 depicts an earmold 1 suitable for use with the proposed invention. The earmold 1 consists of an exterior end 2 with an external opening 4, an insertion end 6 with an insertion opening 8. A peripheral surface 14 forms a seal when inserted into the ear canal. A hollow passageway 10 or duct runs between the external opening 4 and the insertion opening 8, through which sound may pass into the ear canal. The earmold 1 may preferably be made of a flexible material, such as rubber, plastic, or a polymer, although any substance that can be formed to fit sealingly into ear canals of various sizes may be used. The earmold 1 is designed such that, when the passageway 10 is unobstructed, the earmold will provide minimal or no attenuation of external noise within the ear canal. The amount of attenuation provided by an obstructed earmold 1 can vary depending on the properties of the object obstructing the passageway 10. The maximum amount of attenuation that can be provided will depend on several factors, such as the mechanical and acoustical properties of the obstruction, the material properties of the earmold, and the insertion depth of the earmold.

Figure 2:
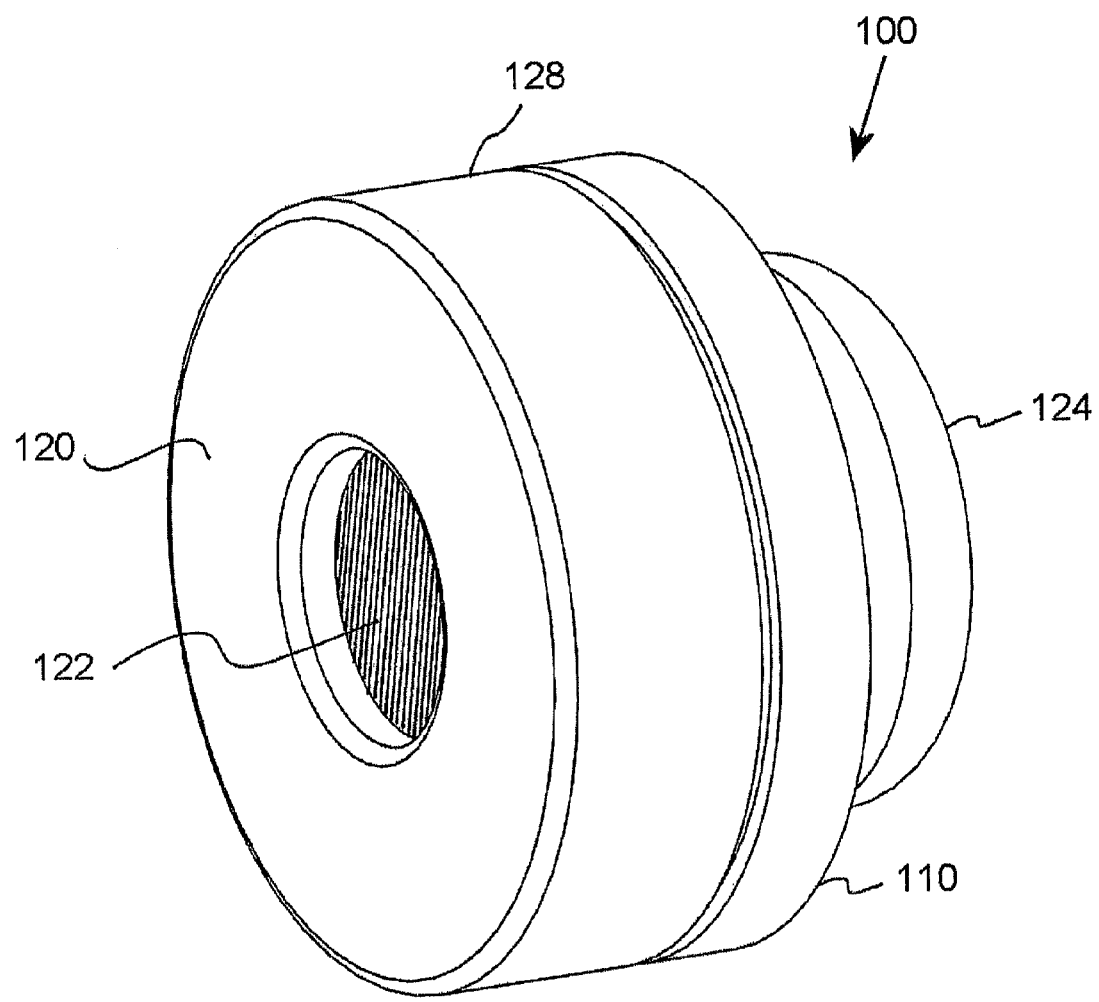
FIG. 2 depicts a perspective view of an ear protector.

The external end 2 of the earmold 1 may be shaped to receive and hold an obstruction, such as an ear protector 100. FIG. 1 depicts an area 12 of the hollow passageway 10 at the external opening 4 to be adapted for holding an obstruction such as the ear protector 100 depicted in FIG. 2 in place.

Figure 3:
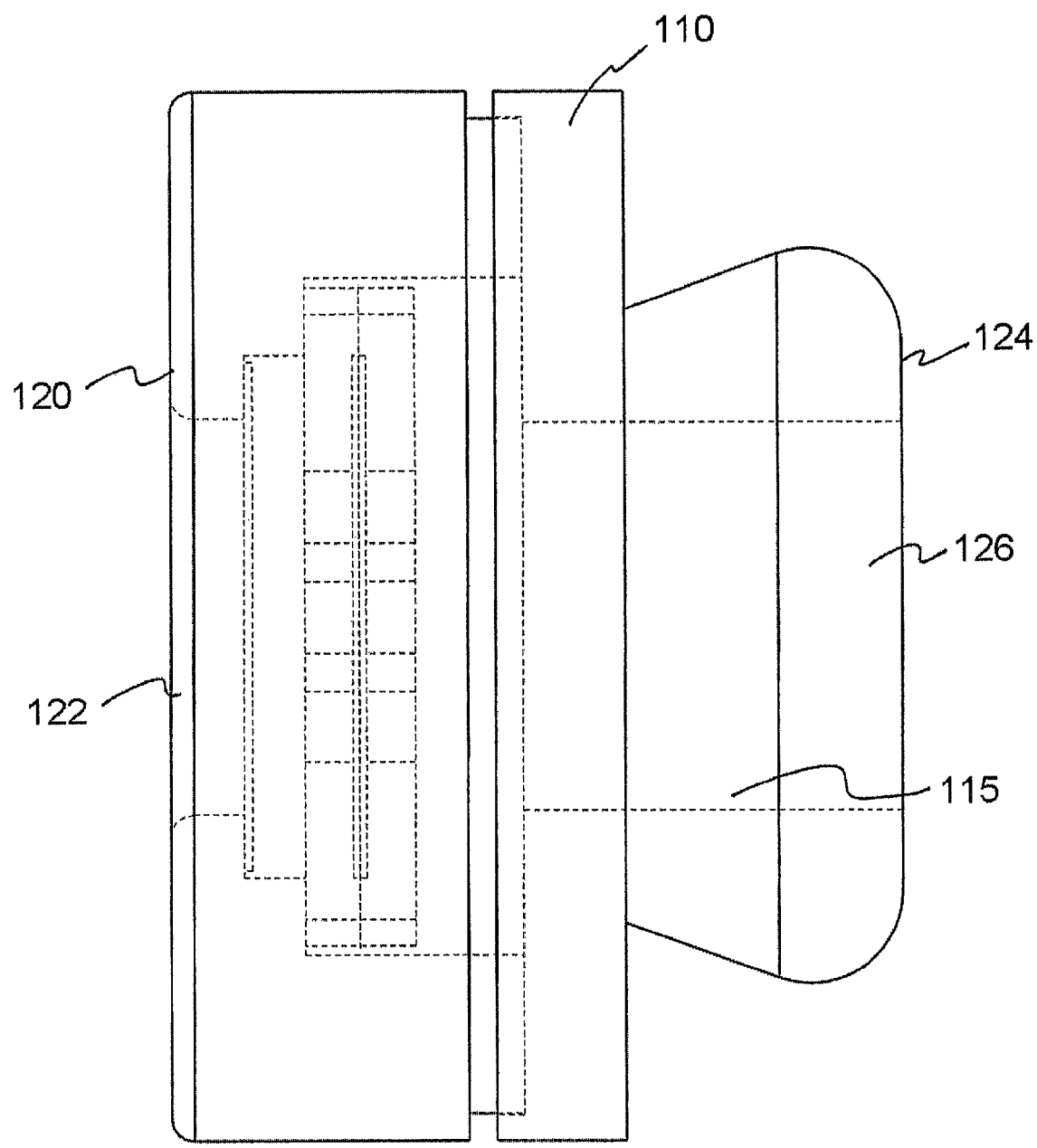
FIG. 3 depicts a side view of the ear protector of FIG. 2 (with the internal structure and objects represented with dotted lines)

FIGS. 2-12 depict various views of an ear protector 100. A housing 110 makes up the external structure of the ear protector 100 and has an external end 120 that faces outward when the ear protector 100 is inserted into an earmold 1 that is inserted into an ear. The housing 110 also has an insertion end 124 that inserts into the earmold 1. The insertion end 124 is preferably narrower than the external end 120 and tapered, as shown in FIG. 3, so that the ear protector 100 may snap in to the flexible external opening 4 of the earmold 1. The ear protector 100 comprises an opening 122 at the external end 120, an opening 126 at the insertion end 124, and a hollow passageway 115 to pass sound to the hollow passageway 10 of the earmold 1 and into the ear canal of a wearer.

Figure 4:
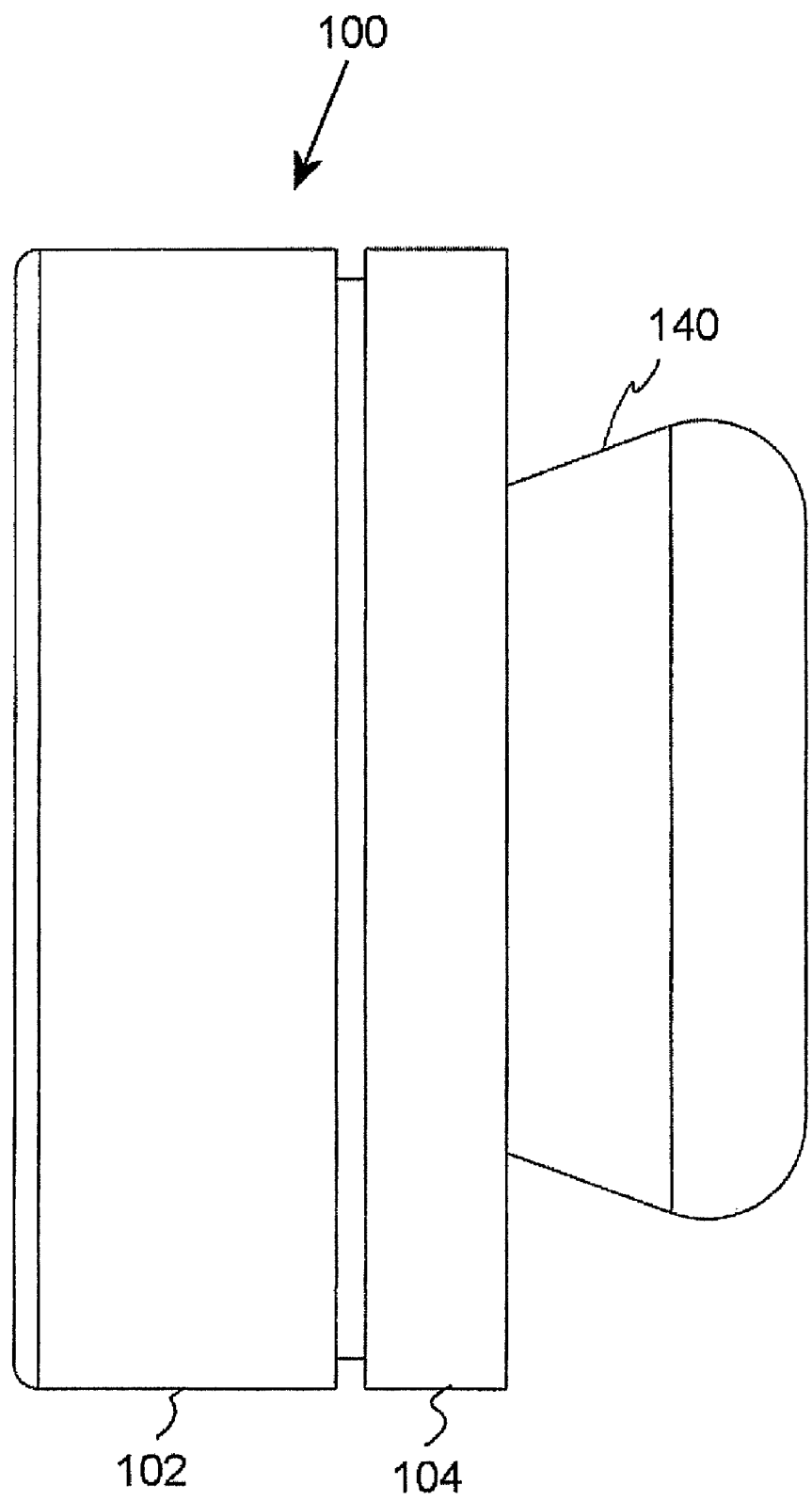
FIG. 4 depicts a side view of the ear protector of FIG. 2.
Figure 5:
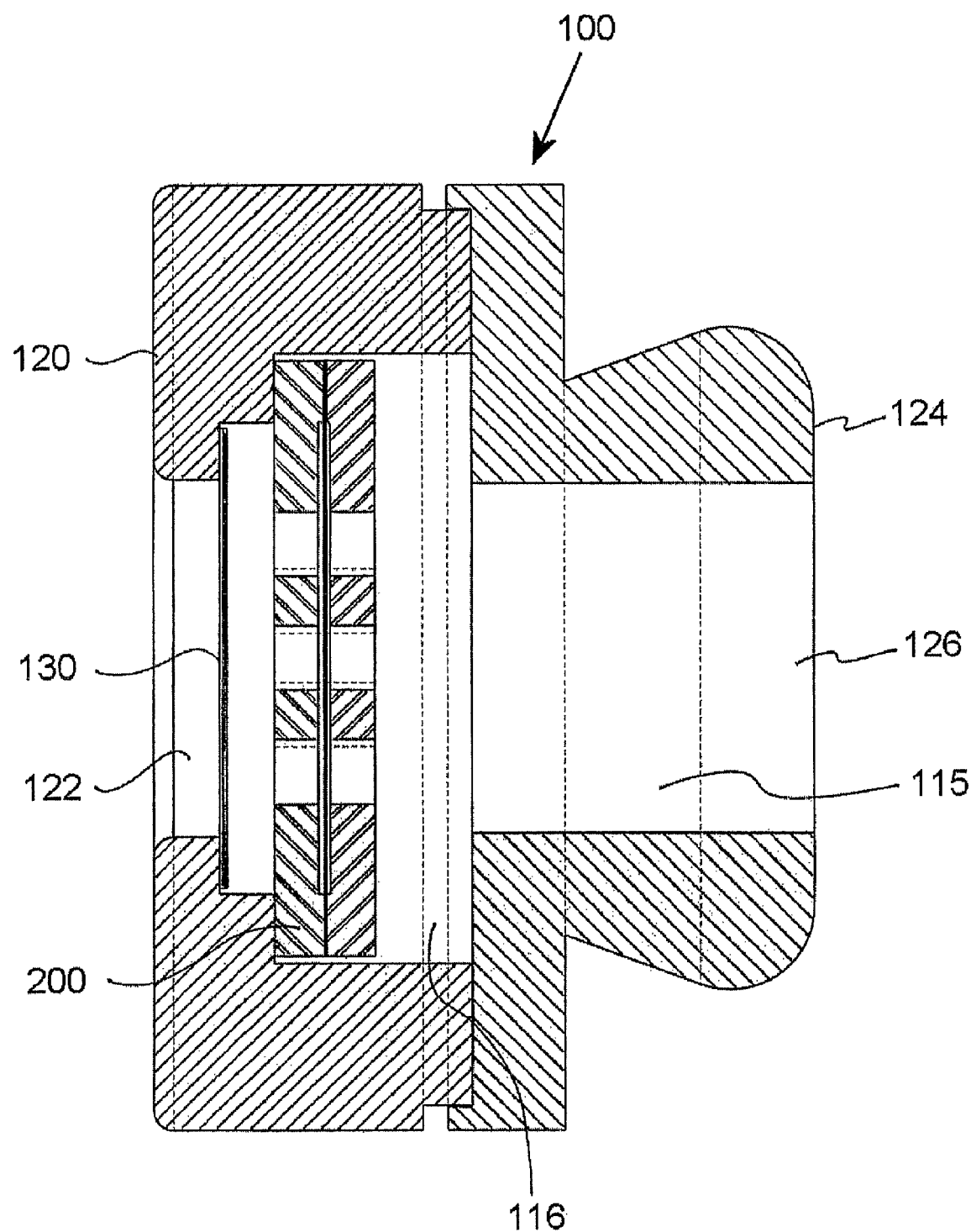
FIG. 5 depicts a cross sectional side view of the ear protector of FIG. 2.

FIGS. 3 and 4 depict side views of the ear protector 100, with FIG. 3 depicting the internal structure and elements of the ear protector 100. FIG. 5 depicts a cross section of a side view of the ear protector 100. A disc 200 is situated within the hollow passageway 115, perpendicular to the direction of travel of sound. Disc 200 attenuates sound that passes through the housing 110, reducing the sound pressure within the ear canal. The structure of disc 200 is depicted in greater detail FIGS. 6-15 and described below.

A damping element or member 130, such as a perforated screen or cloth, extends across the external opening 122 within the hollow passageway 115 of the housing 110. Positioning of the damping member 130 toward the external side of the housing 110, as shown in FIG. 5, tends to protect member 130 from contamination from ear secretion. Note, however, that damping member 130 may also be located adjacent the insertion opening 126 of the housing 110 or at any location within and perpendicular to the passageway 115.

Figure 6:
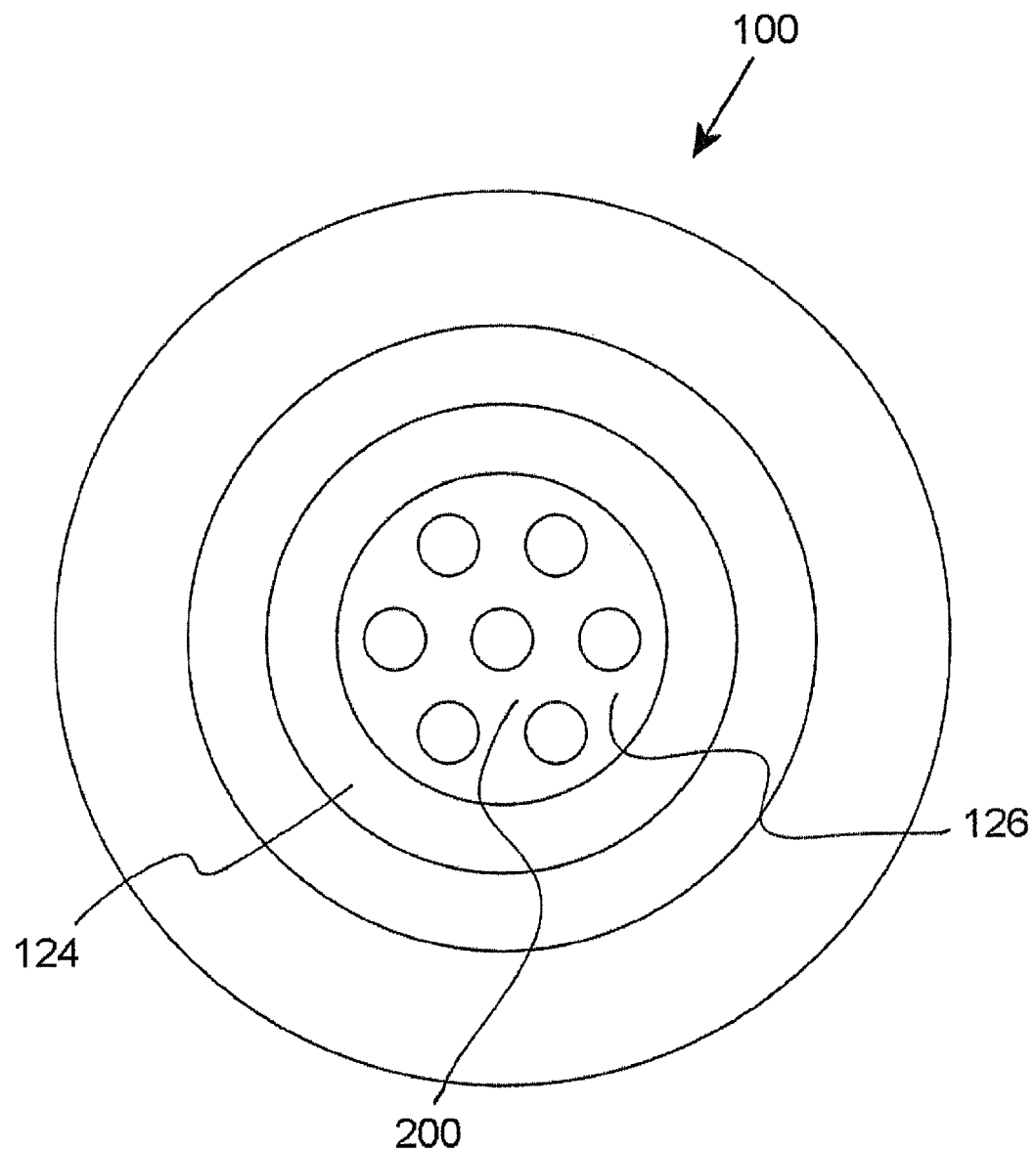
FIG. 6 depicts a view of the insert end of the ear protector of FIG. 2.
Figure 7:
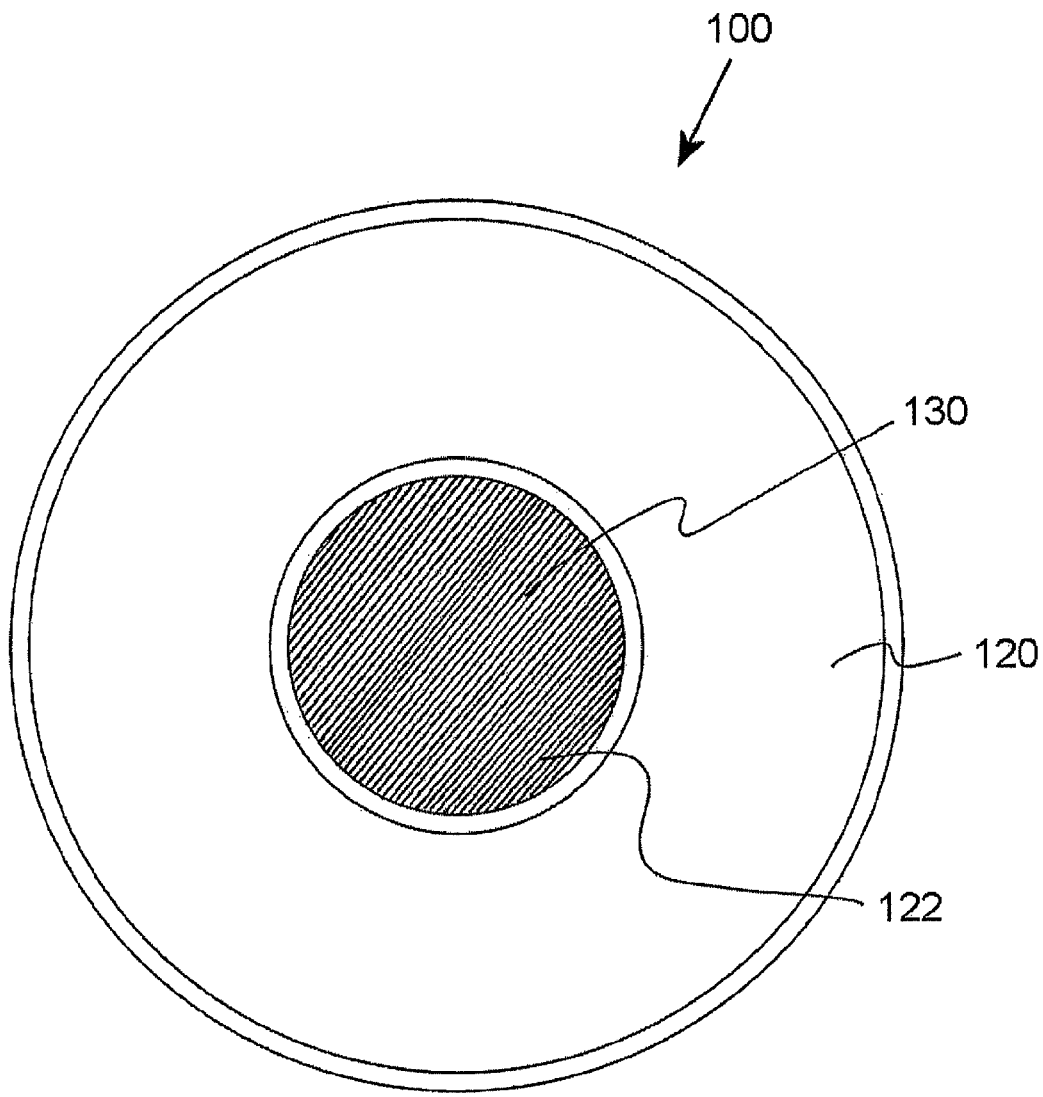
FIG. 7 depicts a view of the external end of the ear protector of FIG. 2.

FIG. 6 depicts a frontal view of the insertion end 124 of the ear protector 100. Looking through the opening 126, the disc 200 can be seen within the hollow passageway 115, shown in FIG. 5. When viewed from the external end 120 of the ear protector 100, as depicted in FIG. 7, damping member 130 is depicted across external opening 122.

Figure 8:
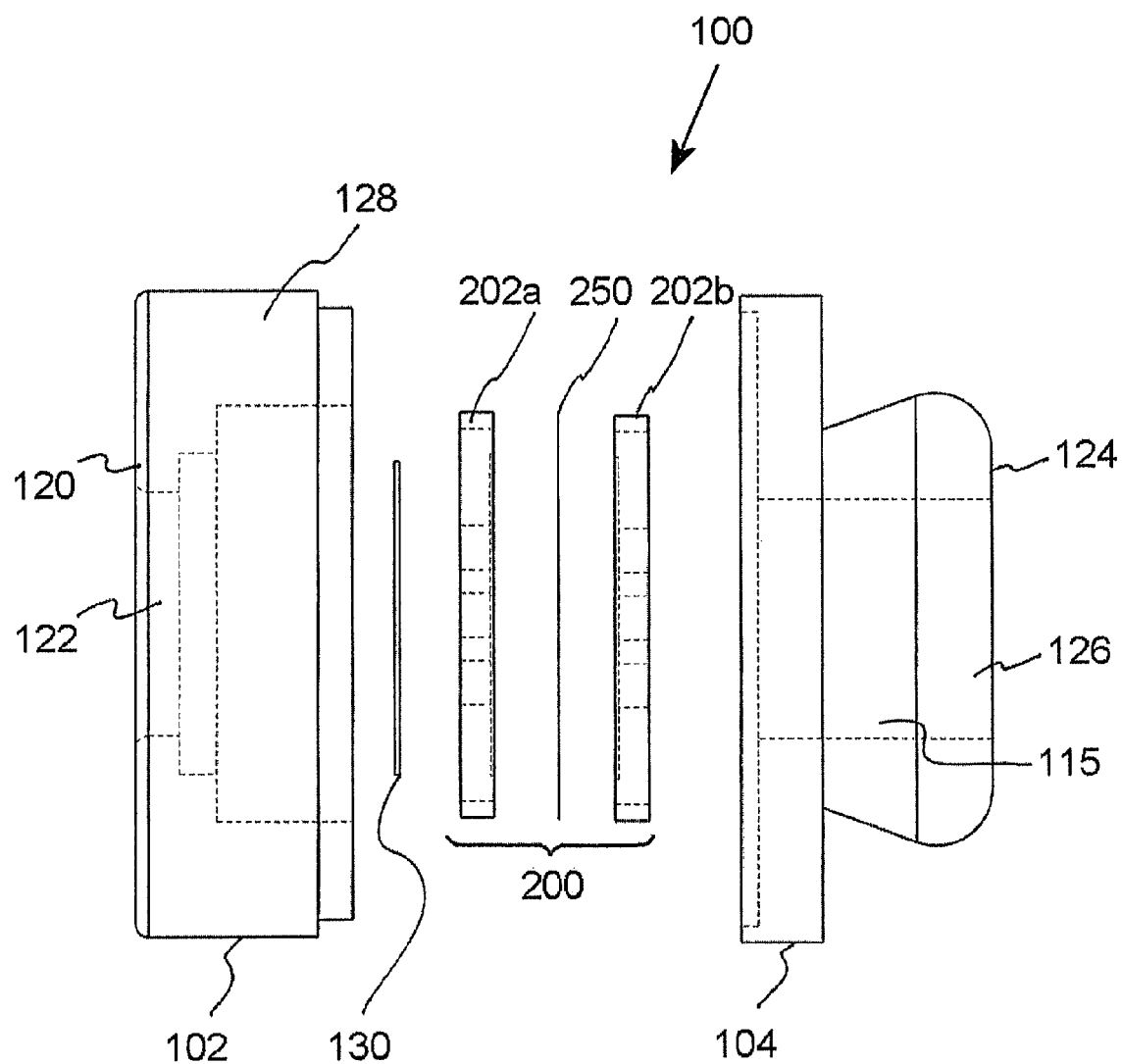
FIG. 8 depicts an exploded side view of the ear protector of FIG. 2.

FIG. 8 depicts the ear protector 100 from the side in an exploded view. In the depicted embodiment the housing 110 is comprised of two components 102 and 104 which fit snugly so as to properly locate them relative to each other together and are glued or welded in place upon assembly to form the housing 110. Disc 200 is comprised of three components, plates 202a and 202b, and a flexible diaphragm 250 situated there between. Damping member 130 is depicted in this embodiment between the disc 200 and the external end 120 of the housing 110. Broken lines depict the internal structure of the housing 110. When assembled, damping member 130 and disc 200 are attached to the housing 110 via a means of adhesion, such as or preferably by solvent bonding.

Figure 9:
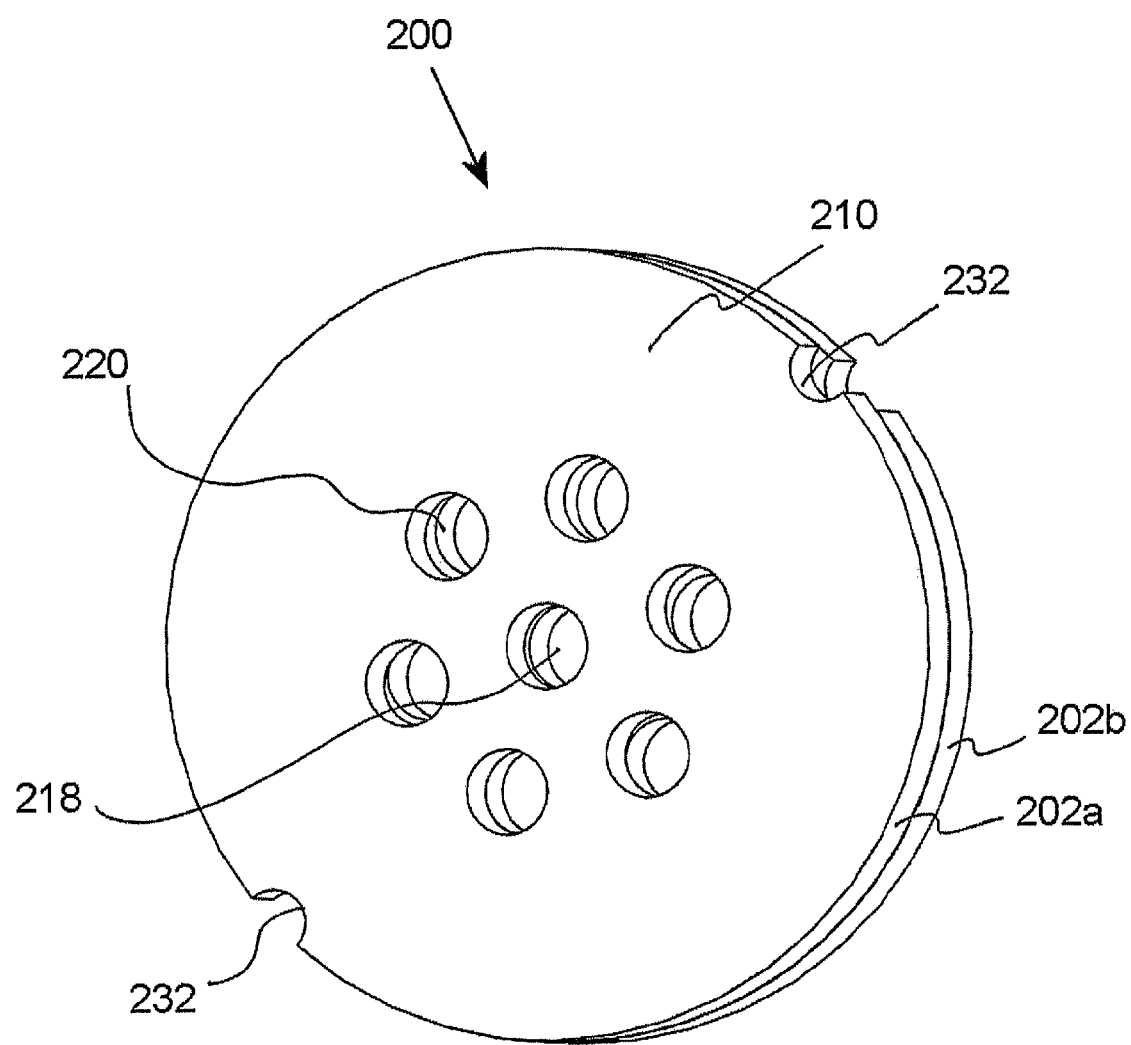
FIG. 9 depicts a front view of a disc of the ear protector of FIG. 2.

FIGS. 9-15 depict various images of the disc 200 removed from the housing 110 of the ear protector 100. FIG. 9 depicts a frontal view of disc 200. In this embodiment a front plate 202a is affixed to a rear plate 202b. The exterior surface 210 of the plate 202 is flat and level. The front and rear plates 202a and 202b are preferably identical in shape and structure, and comprise at least one hole 220 to allow for the passage of sound through the disc. In the depicted embodiment the plates 202a and 202b comprise grooves 232 to aid in the alignment of the plates for assembly. In FIG. 9, the plates are arranged such that non-centered holes of the plates are not evenly aligned. It can be seen in this embodiment that groove 232 of plate 202b is rotated slightly from the groove 232 of plate 202a to achieve the misaligned effect. The interior surface 222 of the plate may be concave or recessed as depicted in FIGS. 10 and 12-14.

Figure 15:
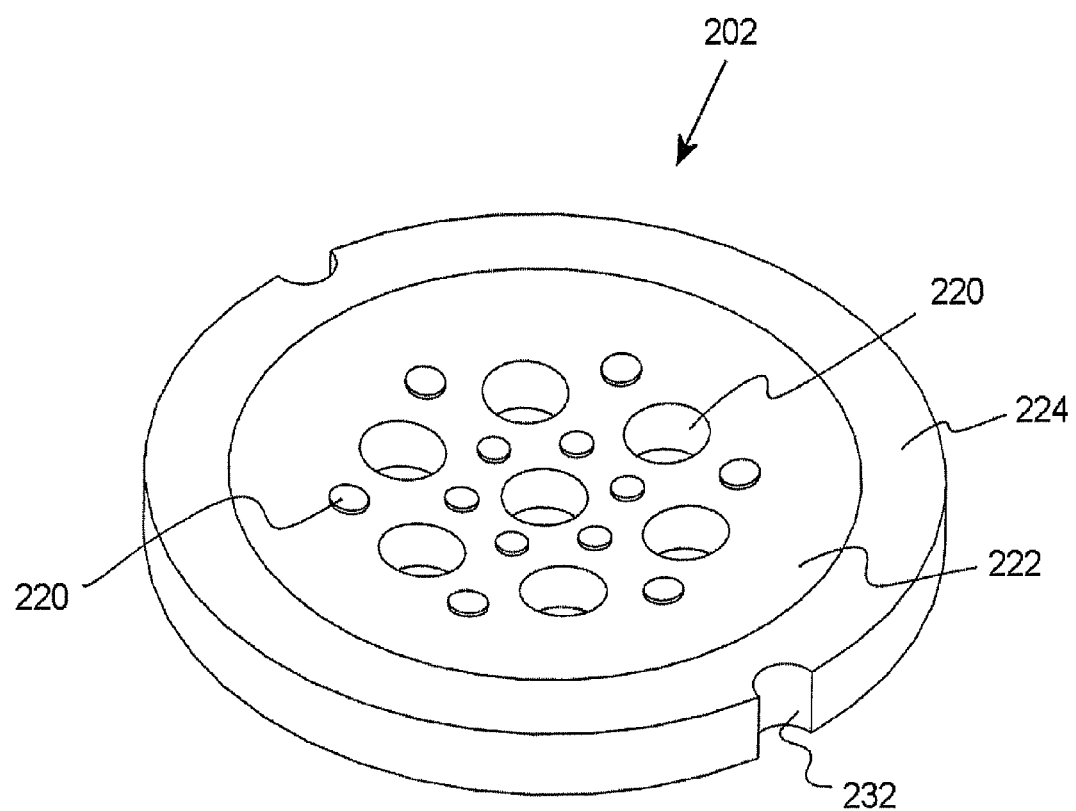
FIG. 15 depicts a perspective view of a plate used in accordance with an alternate embodiment of the present technology.

To achieve a particular attenuation effect (e.g., very low attenuation for sound pressure levels below about 120 dB and a sharp increase in attenuation for sounds above 120 dB), the misalignment angle between grooves 232 of plates 202a and 202b may be modified to range from 0 to 180 degrees. Where the alignment is even (or at 0 degrees), the holes 220 will overlap and thus to reduce attenuation by presenting less obstruction for the flow of sound into the ear. Where the holes are positioned not to overlap, obstruction is increased and thus the attenuation will be greater. For example, to produce a higher level of attenuation at lower external SPLs the plates may be aligned so that there is little overlap between the holes 220 and thus more obstruction for the traveling sound. Conversely, where the desired low level attenuation is minimal, the plates may be aligned such that the holes entirely overlap to provide a direct passage of sound travel through the disc 200. Alternatively, the plates 202 may be configured with holes of various sizes, shapes and locations to achieve various attenuation effects. FIG. 15 depicts an embodiment of a plate 202 with several holes 220 of various sizes configured in a radial-symmetric pattern about the center of the plate 202. This Figure depicts one example of a possible hole configuration for a plate 202 to achieve a particular desired effect.

Though it is preferred that the plates 202a and 202b are identical to simplify and ease in assembly, the invention is not limited to the use of identical plates. For example, plate 202a may comprise a single hole 220 situated in the center of the plate 202a, and plate 202b may comprise two holes 220 situated away from the center of the plate 202b. The use of asymmetric plates may be helpful to achieve a particular attenuation effect for an assembled ear protector 100.

Figure 10:
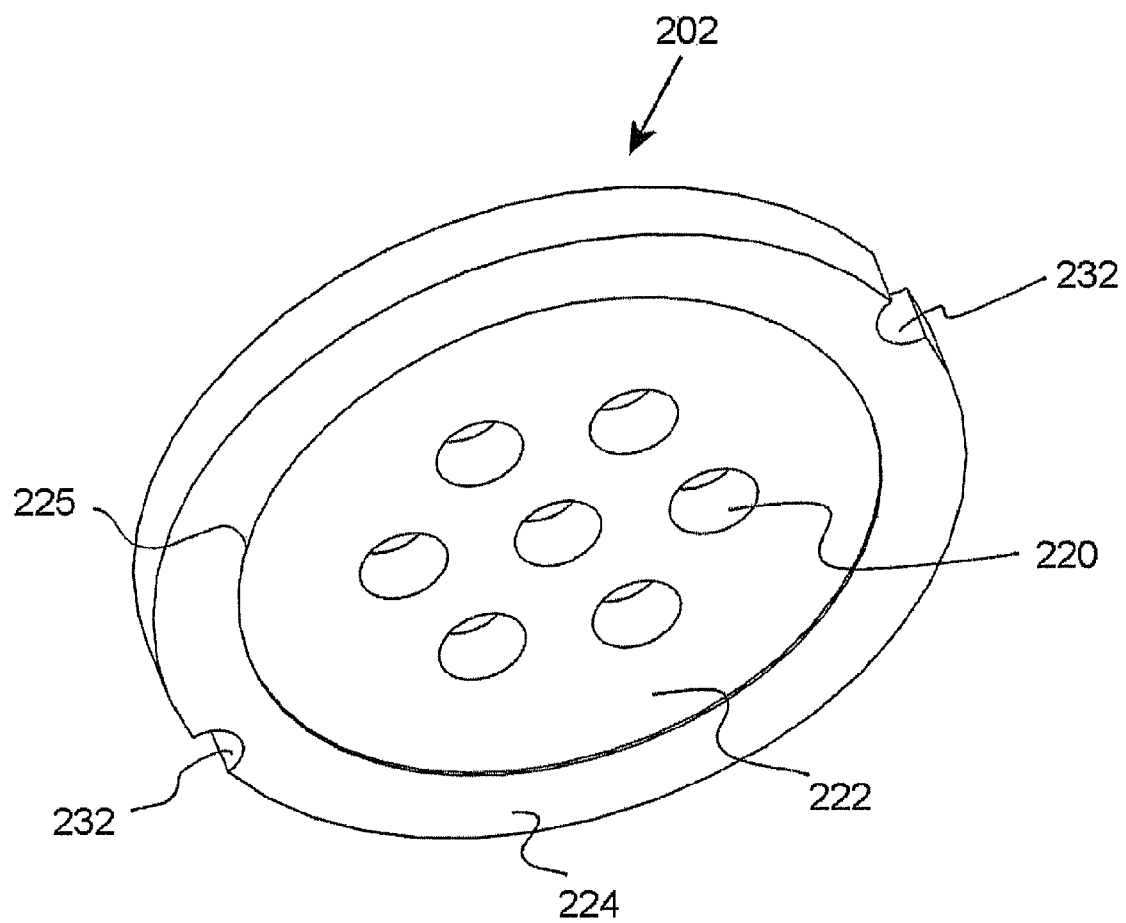
FIG. 10 depicts a perspective view of the internal surface of a plate of the disc of FIG. 9.
Figure 11:
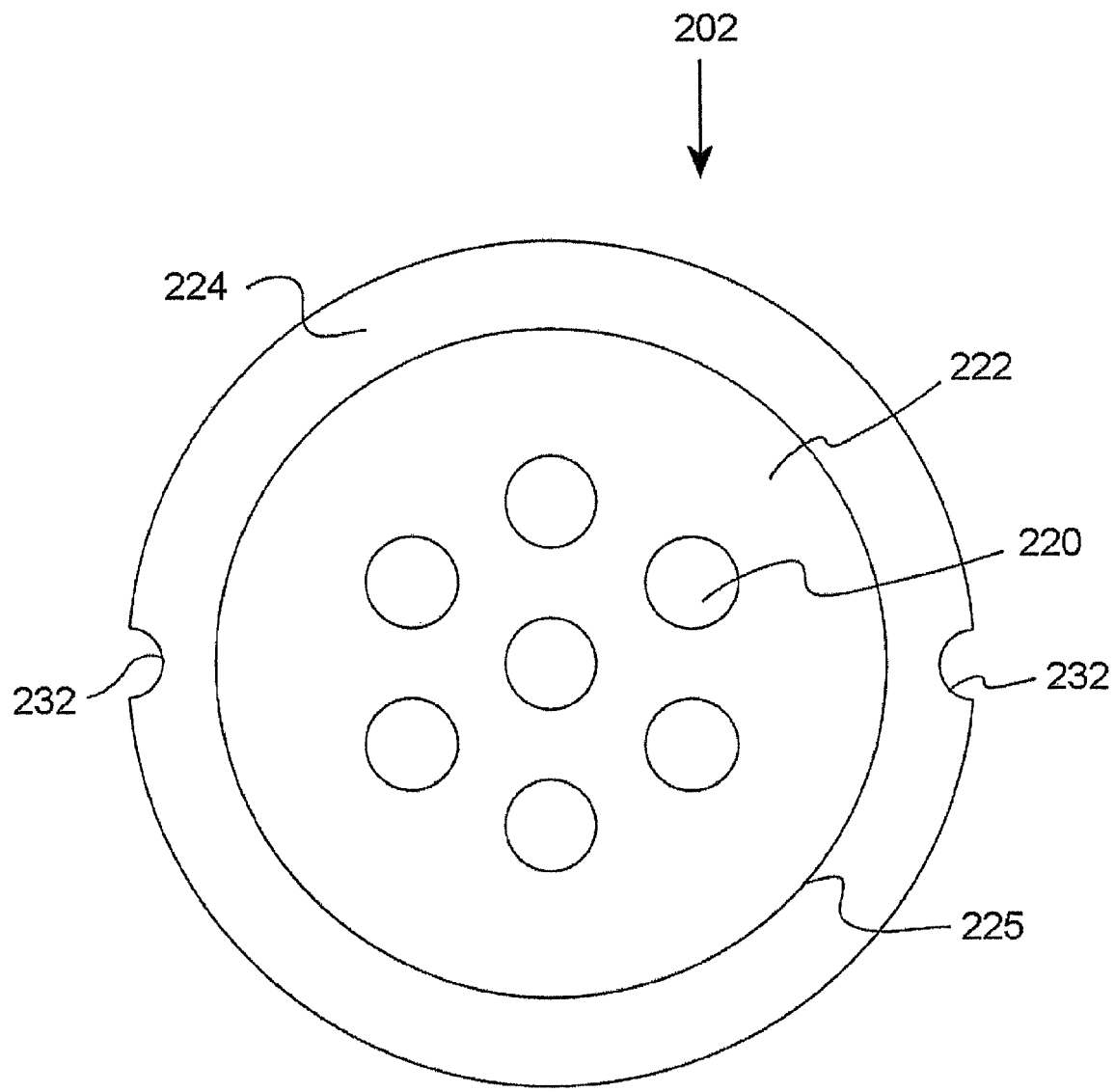
FIG. 11 depicts a front view of the internal surface of the plate of FIG. 10.
Figure 12:
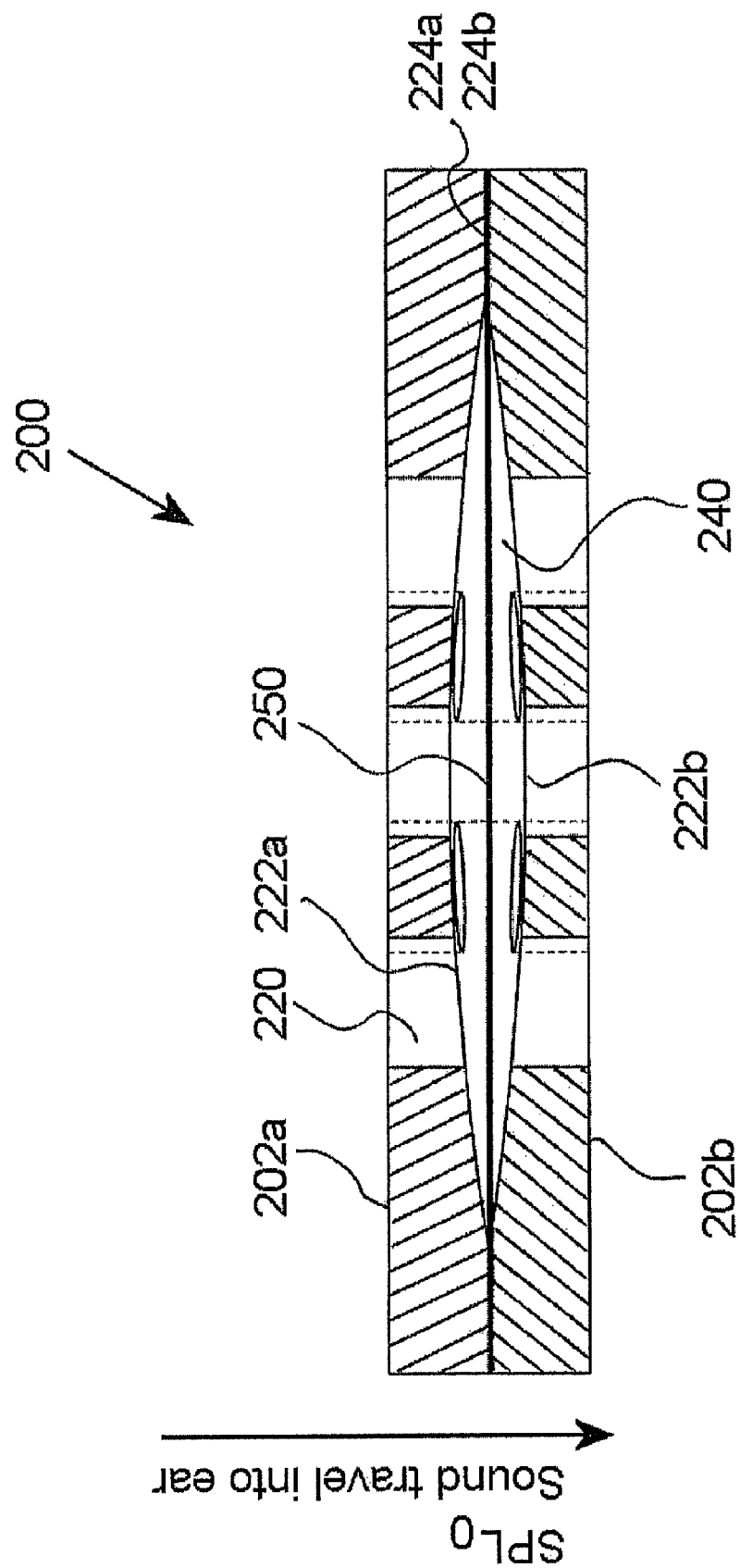
FIG. 12 depicts a cross sectional side view of the disc of FIG. 9 during a low external sound pressure level.
Figure 13:
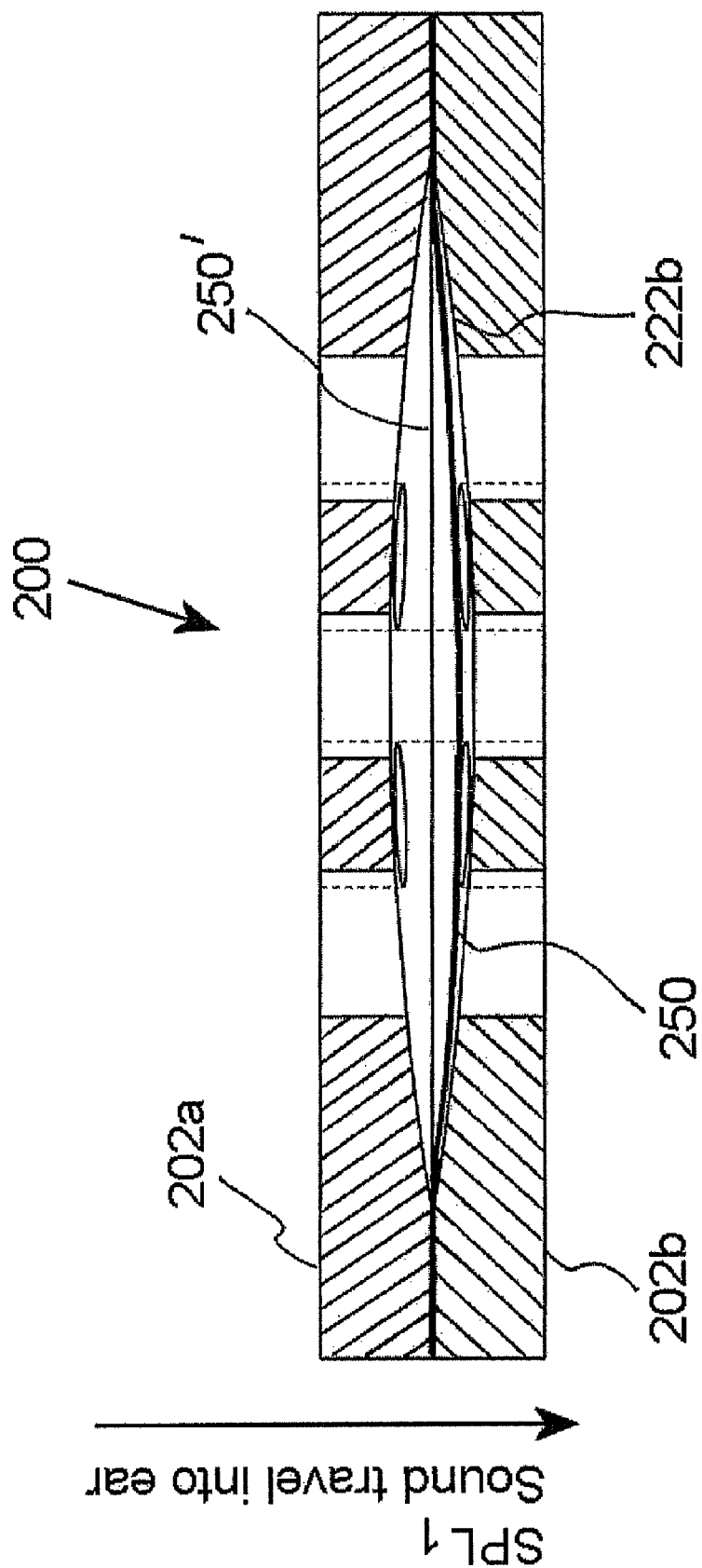
FIG. 13 depicts a cross sectional side view of the disc of FIG. 12 during a moderate external sound pressure level.
Figure 14:
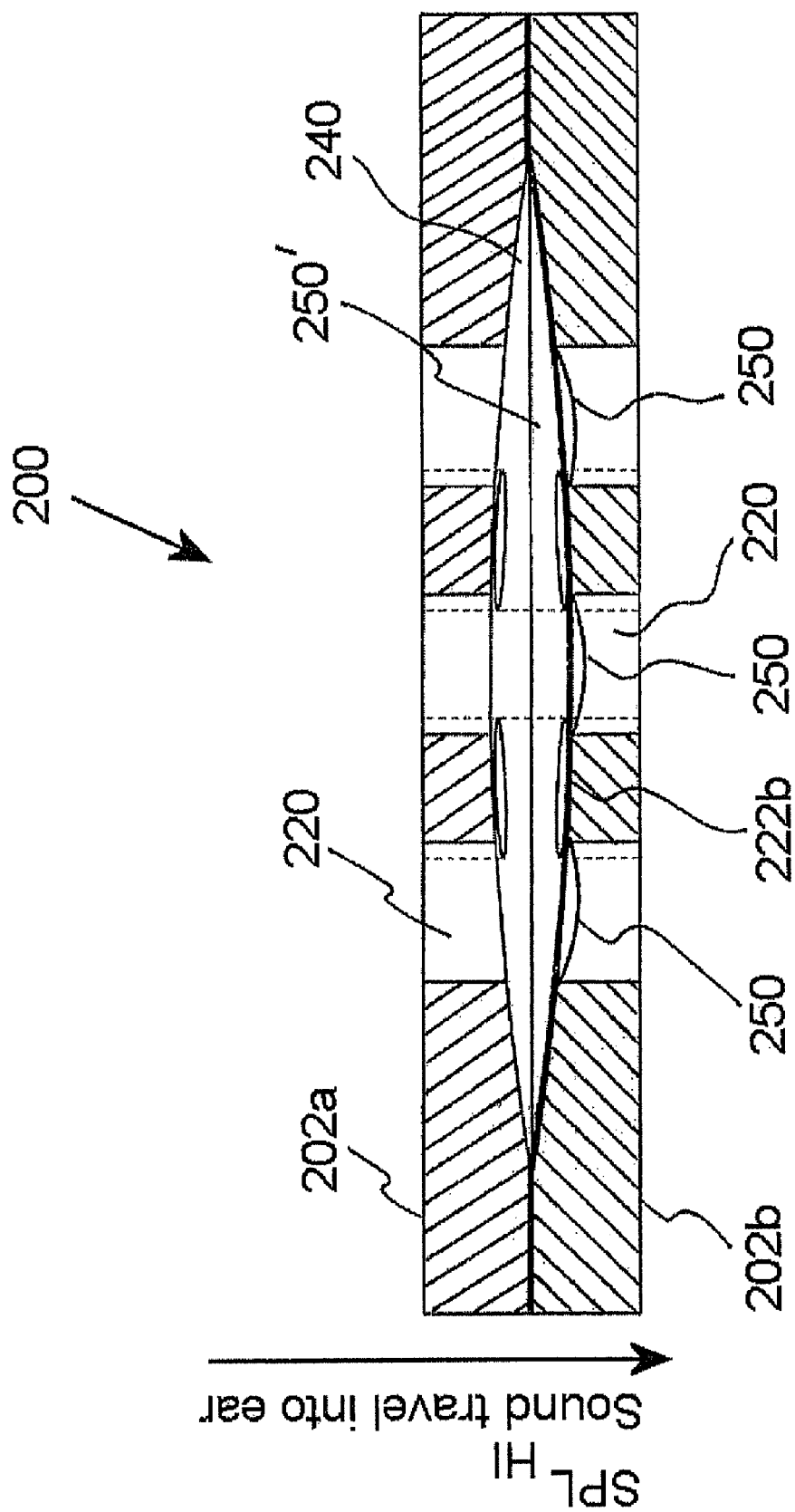
FIG. 14 depicts a cross sectional side view of the disc of FIG. 9 during a high external sound pressure level.

FIGS. 10 and 11 depict views of the interior surface 222 an individual plate 202. Plate 202 may constitute either the front plate 202a or the rear plate 202b of the disc 200. As is seen in FIG. 10, surface 222 is recessed from the rim 224 of the interior side of the plate 202. In the depicted embodiment the interior surface 222 is recessed at the edge 225 of the rim 224 and runs parallel to the surface of the rim 224. In another embodiment, as depicted in FIGS. 12-14, the interior surface 222 is concave. In the concave embodiment the interior surface 222 is recessed further at the center of the plate than at the edge 225 of the surface near the rim 224. In one embodiment the edge of the concave surface 222 may become flush with the edge 225 of 225 of the surface near the rim. The rim 224 of the front plate 202 is flat so that the front plate 202a may contact and lie flush with the rim 224 of the rear plate 202b. When the two plates are adjoined, for example, with adhesive bonding, the recessed interior surfaces 222 establish a cavity 240 within the disc 200.

FIGS. 12-14 depict a cross sectional view of the assembled disc. In the depicted embodiment the recessed interior surfaces 222 of the plates 202 are concave, and the edges of the concave surfaces 222a and 222b are flush with the edges 222a and 224b of the rim. When assembled the concave surfaces 222 establish a cavity 240 within the disc. FIGS. 12-14 are not drawn to scale. The size of the cavity 240 has been enlarged with respect to the size of the disc 200 as compared to the preferred embodiment to demonstrate the effects of the cavity 240 on the sound attenuation.

Situated between the plates 202a and 202b is a thin, flexible diaphragm 250 that flexes with under pressure. The diaphragm 250 may be made of extremely thin polyethylene or Teflon foil, for example, however, the diaphragm 250 is not intended to be limited to the described materials. It is preferred that the shape of the cavity 240 of the disc 200 matches the shape of the diaphragm 250 when flexed such that the diaphragm 250 will uniformly contact the entire interior surface 222 when flexed to the point of contact. Though preferred for a particular application ear protector 100, it is not intended that the ear protector 100 be limited to such an embodiment as other cavity shapes can be used to produce other sound attenuation effects. For example, the interior surface 222 may be recessed to create a cylindrical shaped cavity 240 where the surface 222b runs parallel to the rim 224 as depicted in FIG. 10.

FIG. 12 depicts the disc at minimal SPL. In this embodiment the diaphragm 250 is unflexed and in a position parallel to the disc itself. FIG. 13 depicts an embodiment with an increase in exterior sound pressure. Here the increased pressure has caused the diaphragm 250 to flex beyond its unflexed position 250', but not to the point where the diaphragm 250 has come into contact with the interior surface 222b of the rear plate 202b. At this position the disc 200 provides a relatively low and constant level of attenuation, allowing the sound to pass through the diaphragm 250 and the holes 220 and into the ear canal. FIG. 14 depicts a cross sectional view of the disc where the SPL is large enough so that at the pressure peak of the sound waveform, the diaphragm 250 is caused to to flex to the point of contact with interior surface 222b of the rear plate 202b. With proper design of the concave surface 222 of disk 202, at a certain pressure, the diaphragm 250 will have covered each of the holes 220 of the disc and thus provided a restriction on the flexibility of the diaphragm. In particular, the proper shape of surface 222 will match the shape of the deflected diaphragm 250. As the SPL increases further, the portion of the time that the motion of diaphragm 250 is restrained against interior surface 222 increases. The portion of the diaphragm 250 that is over the holes 220 may further flex within the open space behind each hole as depicted in the diagram. Since the diameter of each of the holes 220 is small compared to the diameter of cavity 240, the flexing of diaphragm 250 within the holes 220 is substantially less than the free flexing of diaphragm 250, thereby rendering a higher impedance to the passage of sound. For example, in one embodiment, the holes 220 may be about 0.0026 inches in diameter, wherein the diameter of the diaphragm 250 and/or the diameter of the cavity 240 is about 0.190 inches in diameter. It is at the SPL where the diaphragm 250 contacts the interior surface 222 of the rear plate 202b that the level of attenuation of the ear protector 100 increases significantly and non-linearly. Accordingly, the shape of the plates 202 and the size of the cavity 240 may be customized such that the non linear attenuation affect is achieved at various SPLs.

Figure 16:
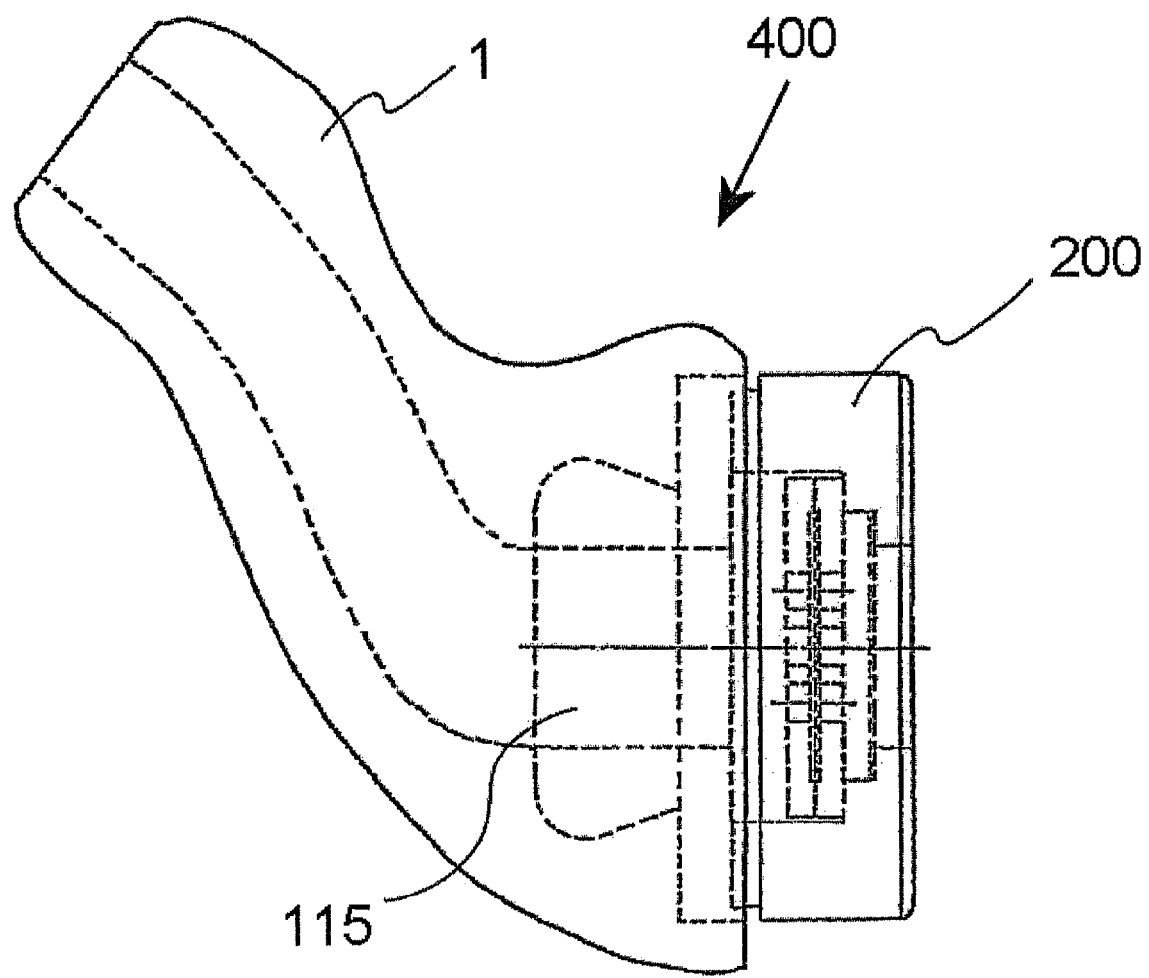
FIG. 16 depicts a side view of the ear protector of FIG. 2 inserted into the earmold of FIG. 1 (with internal structure represented with dotted lines)

FIG. 16 depicts the complete assembly of the ear protector 400 of the ear protector 200 as inserted into an earmold 1. When inserted into the ear canal the ear protector may provide a minimum attenuation that is negligible, and a maximum attenuation up to that provided by a solid earmold 1.

One object of the inventive ear protector is to provide high audibility across all frequency ranges for low external SPLs. In other words, where the external SPL is below a predetermined amount, the ear protector provides a near constant attenuation across the entire spectrum of audible sound frequencies. To provide low levels of attenuation within the ear canal the diaphragm 250 operates as described in U.S. Pat. No. 4,807,612 issued to Carlson to provide a low and uniform attenuation across frequency.

Refer now to FIGS. 17A and 17B. The natural resonance of the ear canal shapes the frequency-amplitude characteristic of the sound pressure delivered to the eardrum. When the ear is obstructed by an attenuating plug the natural resonance in the ear canal is significantly altered. One feature of the inventive ear protector is to provide an acoustical network for reconstructing this natural resonance-dependent relationship when a protector is positioned in the user's ear canal, following the teaching of the Carlson patent.

Figure 17:
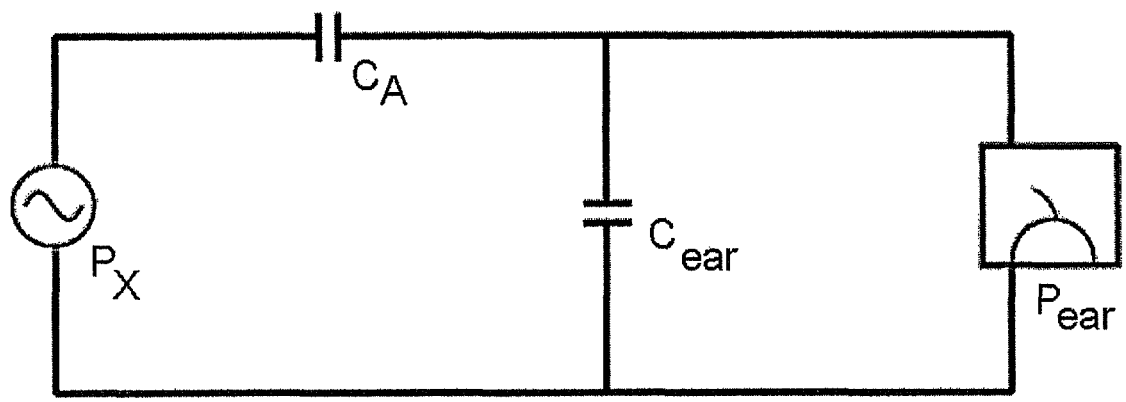
FIG. 17 is a schematic of a circuit used in accordance with an embodiment of the present technology.

Referring to the low-frequency equivalent circuit FIG. 17, the acoustic compliance of the diaphragm 250 acts as a pressure divider with the acoustic compliance of the ear, comprising the volume of the ear canal and the compliance of the eardrum. The sound pressure in the ear canal will be related to the incident pressure Px by equation 1, as is well known by those of ordinary skill in the art.

$$P_{ear} = P_x \left( \frac{C_A}{C_A + C_{ear}} \right) \qquad [\text{eq. 1}]$$

Thus, the pressure across the ear equals the product of the external pressure and the ratio of the diaphragm compliance to the complete circuit compliance divided by the added compliance values of the diaphragm and the ear. Accordingly, a smaller value for diaphragm compliance will lead to a smaller pressure within the ear canal or, a greater value of attenuation.

The total amount of attenuation can be calculated using the following equation, calculated in decibels (dB):

$$A = 20 \times \log(P_{ear}/P_x); \qquad [\text{eq. 2}]$$

$$\text{or } A = 20 \times \log\left(\frac{C_A}{C_A + C_{ear}}\right); \qquad [\text{eq. 3}]$$

Where A represents the decibel level of sound attenuated, the acoustic compliance of the portion of the ear ear beyond the earplug is roughly 1 cgs acoustic μF. An attenuator diaphragm with a compliance of 0.25 μF will thereby provide a pressure ratio within the ear canal of about ⅕ that of the external SPL. Using eq. 3, this translates roughly to an attenuation of 14 dB. An attenuator diaphragm with a compliance of 0.1 μF will translate roughly to 21 dB of attenuation.

Figure 18:
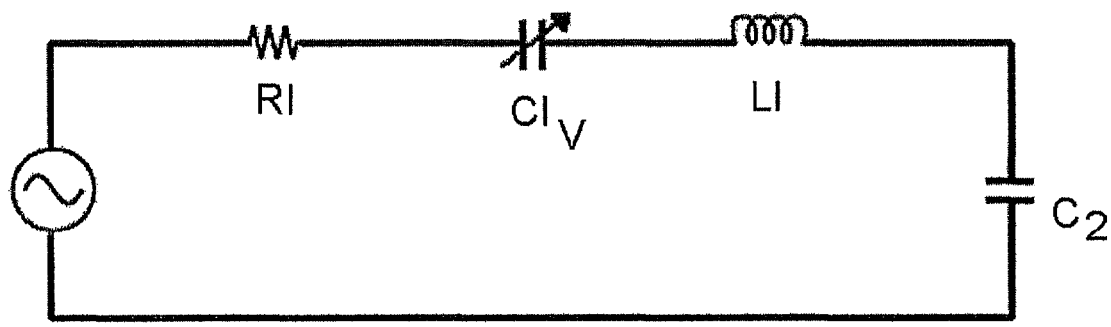
FIG. 18 is a schematic of a circuit used in accordance with an embodiment of the present technology.

In general, the stiffer the diaphragm, the lower the acoustic compliance will be and therefore, the higher the level of attenuation. The ear protector described provides a level-dependent attenuation resulting from the level-dependent compliance of the system. This is depicted in the simplified equivalent acoustic circuit shown in FIG. 18. The circuit of FIG. 18 includes the acoustic mass of the sound channel 115 and the resistance 130. The level-dependence of compliance $C1v$ in FIG. 18 provides for lower levels of attenuation at lower external SPLs and higher levels of attenuation at higher external SPLs. For example, at an external SPL of 60 dB the value of $C1_v$ may be at a higher value, perhaps 1 μF. This would yield an attenuation of approximately 6 dB. At a higher SPL of 140 dB, the value for $C1_v$ may dramatically drop, perhaps to a value of 0.01 μF, and yield a much higher attenuation of 40 dB.

Through the operation of providing increased attenuation at higher external SPLs as the compliance of the diaphragm decreases at higher external SPLs. This affect may be achieved by restricting the responding change in volume of the passageways 10 and 115 during an increase in pressure. The ear protector can achieve this effect by increasing the stiffness, thus inhibiting the displacement of the diaphragm at higher SPLs. One method to achieve this effect is to provide a rigid backstop which inhibits the flexibility of the diaphragm from flexing beyond a certain point. Refer again to FIGS. 12-14. FIG. 12 depicts the diaphragm 250 situated within the cavity 240 of the disc 200. In this embodiment the external SPL (identified here as $SPL_0$) is minimal or nonexistant and the diaphragm 250 is un-flexed. An increase in sound pressure causes the diaphragm 250 to flex beyond the un-flexed position 250', as depicted in FIG. 13. In the embodiment depicted in FIG. 13, though the increase in external SPL (identified here as $SPL_1$) from $SPL_0$ causes the diaphragm 250 to flex, the diaphragm 250 does not flex enough to encounter the interior surface 222b of the rear plate 202b. Accordingly, at this SPL the stiffness of the diaphragm 250 has not changed, nor has the flexibility of the diaphragm 250 been inhibited from that of the low sound pressure level of FIG. 12. The amount of attenuation thus remains relatively constant between the embodiments.

FIG. 14 depicts the interior of the disc 200 at a high exterior SPL (identified as $SPL_{HI}$). At $SPL_{HI}$ the external sound pressure causes the diaphragm 250 to contact the interior surface 222b of the rear plate 202b. The surface 222b of the plate 202b prevents the flexibility of the diaphragm 250 beyond the surface 222b. At this SPL and for SPLs above this point the flexibility of the diaphragm 250 is limited to the locations where it contacts the holes 220 of the plate 202b. The inhibition of flexibility of the diaphragm causes a decrease in the compliance resulting in a higher level of attenuation provided by the ear protector.

In FIG. 14 the diaphragm 250 can be seen flexed beyond the interior surface 222b at the holes 220 of the disc 200. The combined area of the holes 220 may be significantly less than the entire surface area of the exposed diaphragm 250. As a result the change in volume of the passageways 10 and 115 (the value of ΔV from eq. 7) caused by a pressure increase will be significantly less for external SPLs above $SPL_{Hi}$ than for lower SPLs. Recall from equation 7 that the value of compliance for the ear protector is the change in volume over the pressure, or ΔV/P. Thus, where the flexible surface area of the diaphragm 250 is restricted to the areas of the holes 220, the value of ΔV will be significantly lower, variably reducing the compliance of the ear protector 100 and thus, increasing the attenuation.

The size and shape of the cavity 240, and the size, number and location of holes 220 may be modified in various embodiments to establish various levels of $SPL_{Hi}$ for different ear protectors 100. For example, a ear protector may be designed to operate with a value of $SPL_{Hi}$ at 140 dB, such that very little sound below an SPL of 140 dB is attenuated. Such an ear protector will have, among other things, a larger cavity 240 than one which is designed to operate with a value of $SPL_{Hi}$ at 100 dB.

In certain embodiments of the present technology a triboelectric charge may be formed as the diaphragm 250 rubs against the surface 222 of the assembly 200. Experiments were conducted to reduce potential issues that may be caused as a result of this triboelectric charge, for example, the diaphragm 250 sticking to the surface 222 of the assembly 200 after contact, thereby causing "hang-ups" after a high-attenuation state. Accordingly, certain embodiments of the present technology introduce a thin aluminum film to the diaphragm 250. Additional embodiments introduce a metallization to the surface 222 instead of, or in addition to the aluminum film applied to the diaphragm 250. The aluminum film and the metalized surface 250 are designed to not significantly affect (e.g., decrease) the compliance of diaphragm 250, while sufficiently reducing the charge buildup to reduce the likelihood that the diaphragm 250 remains in contact with the surface 222 after a high SPL is provided.

Figure 19:
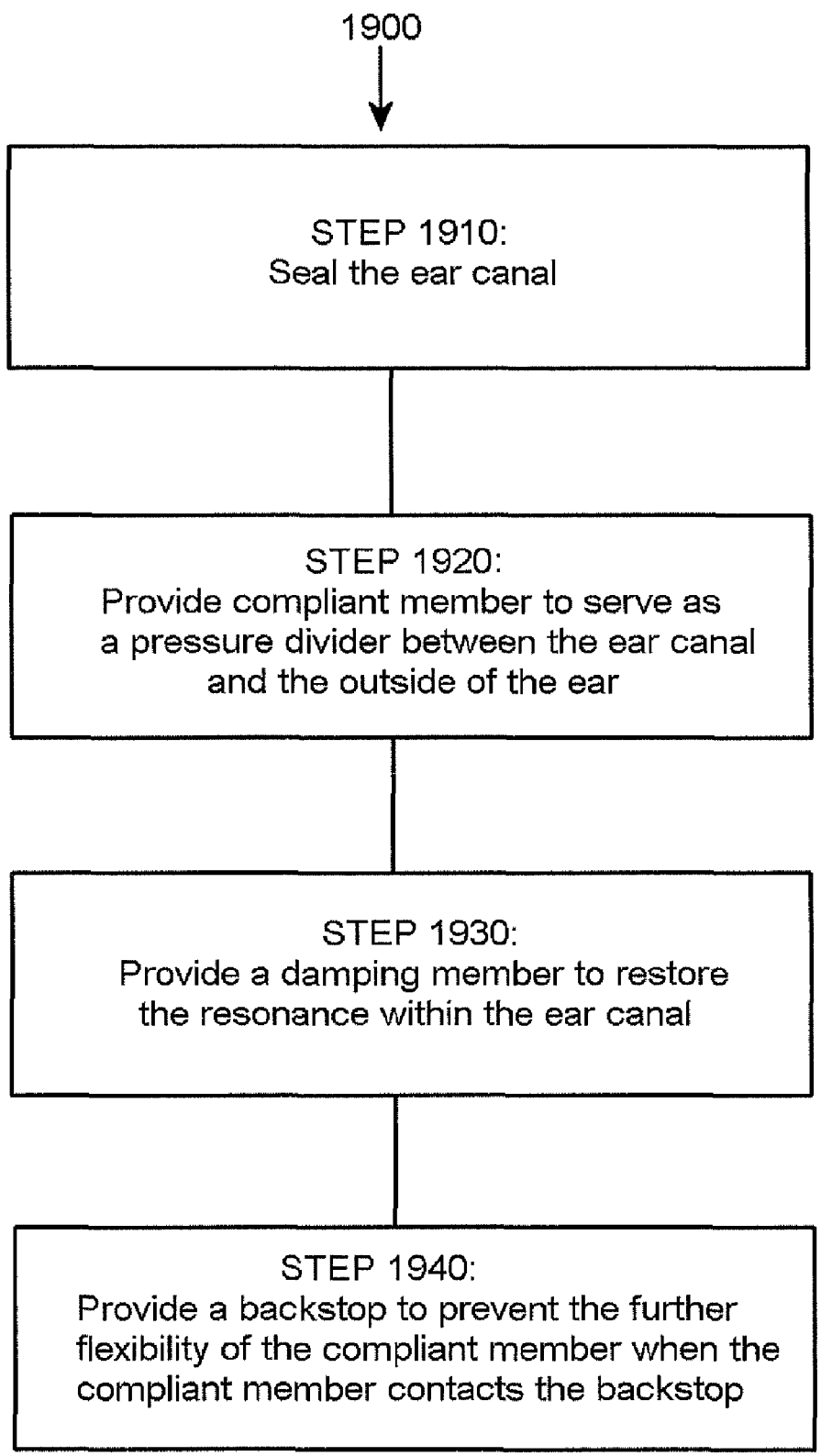
FIG. 19 is a flow diagram depicting an embodiment of a method practiced in accordance with the present technology.

Certain embodiments of the present technology provide methods for reducing sound in the ear canal. FIG. 19 depicts a method 1900 for reducing sound within the ear canal such that the level of sound attenuated depends upon the sound pressure level of sound external to the ear canal. Method 1900 comprises the following steps:

Step 1910: In this step the ear canal of is sealed with a plug such as an earmold 1, or a housing 110 to direct the flow of sound from outside the ear into the ear canal through a passageway within the plug such as passageway 10 of earmold 1.

Step 1920: In this step sound passing through the passageway into the ear canal is attenuated by a compliant member, for example, flexible diaphragm 250 of FIGS. 12-14. In this step an increase in sound pressure causes compliant member to flex and thereby establish a change in volume within the passageway and the ear canal. In this step the compliant member serves as a pressure divider and thereby has the effect of transforming the ear canal into an essentially closed resonator and effectively destroys the resonance of an unobstructed ear canal.

Step 1930: In this step a damping member 130 is provided for supplying an acoustical resistance that restores the resonance within the ear canal destroyed by the compliant member.

Step 1940: In this step a backstop is provided within the plug behind the compliant member, in the direction of sound travel into the ear. The backstop prevents the flexing of the compliant member in locations where the compliant member contacts the backstop. This backstop may an interior wall of a disc that houses the compliant member, for example, surface 222b of disc 200 of FIGS. 12-14. The backstop comprises one or more holes to allow for a free flow of sound at low SPLs.

Where the sound pressure external to the ear is great enough to cause the compliant member to contact the backstop the attenuation provided by method 1900 is greater than where the sound pressure has not caused the compliant member to contact the backstop.

In operation, the operative ear protector 100 works as follows. An earmold 1 provides a seal of the ear canal into which the ear protector 100 may be inserted. A damping member 130 and a perforated disc 200 are located within the ear protector 100. The disc 200 contains a cavity 240 and a flexible diaphragm 250 within the cavity 240. The damping member 130 preserves the frequency characteristic (or resonance) that the eardrum normally experiences in the presence of an attenuator such as diaphragm 250. Thus, the sound delivered to the eardrum is substantially that which would have been observed at the eardrum in the absence of the attenuator decreased by a factor. At low SPLs, the diaphragm 250 within the disc 200 flexes with a change in sound pressure, attenuating external sound at a constant and relatively lower amount. A soldier in combat wearing such a device, for example, will be able to detect necessary low level noises, such as an approaching enemy. At a predetermined external sound pressure level, the sound pressure causes the diaphragm 250 to flex to a point where it contacts the interior surface 222b within the cavity 240 of the disc 200. At and above this SPL the flexibility of the diaphragm 250 is impeded by the presence of the interior wall 222b. The flexibility of the diaphragm 250 is limited to its location at the holes 220 of the plate and is thereby dramatically reduced. This reduction in flexibility creates a decrease in acoustical compliance of the ear protector 100 and an increase in the level of attenuation provided by the ear protector 100. The ear protector 100 attenuates loud and potentially eardrum-damaging sounds to safer levels for the duration of the blats, then returns to a low attenuation level once the environment has quieted. The ear protector 100 protects the wearer's ears without blocking desirable sounds.

While the present technology has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims.

What is claimed is:
1. A non-linear sound attenuator comprising:
 a. a housing comprising a hollow passageway for passing external sound through the insert into the plug; and
 b. an attenuating disc interposed across the hollow passageway of the housing, said attenuating disc comprising:
  i. a cavity comprising an interior surface;
  ii. at least one hole through said disc; and
  iii. a flexible diaphragm positioned across the hollow cavity;
whereby sound pressure causes the flexible diaphragm to expand, and whereby the flexible diaphragm contacts the interior surface of the cavity at a sound pressure level at or greater than that of a peak value, thereby restricting the flexibility of the diaphragm at sound pressure levels above the peak value.

2. The non-linear sound attenuator of claim 1, wherein the interior surface of the cavity is of a shape to match the shape of the flexible diaphragm when the diaphragm is expanded.

3. The non-linear sound attenuator of claim 2, wherein the interior surface of the cavity has a concave shape.

4. The non-linear sound attenuator of claim 1, further comprising a damping member situated within the housing.

5. The non-linear sound attenuator of claim 1, wherein the at least one hole through said disc is small compared to the size of the cavity.

6. The non-linear sound attenuator of claim 5, the cavity having a diameter, wherein the diameter of the at least one hole is about 0.0026 inches and the diameter of the cavity is about 0.190 inches.

7. The non-linear sound attenuator of claim 1, wherein the attenuator provides a greater sound attenuation for external sound pressure levels above the peak value than for external sound pressure levels below the peak value.

8. The non-linear sound attenuator of claim 7, wherein the peak value is approximately 150 dB.

9. The non-linear sound attenuator of claim 7, wherein the peak value is approximately 110 dB.

10. A non-linear sound attenuator for insertion into an ear canal comprising:
 a. a plug for sealing the outer portion of the ear canal comprising a hollow duct for passing external sound through the plug into the ear canal; and
 b. a plug insert removably inserted within the plug at an opening of an external end of the plug, the plug insert comprising:
  i. a housing comprising a hollow passageway for passing external sound through the insert into the plug; and
  ii. an attenuating disc interposed across the hollow passageway of the housing, said attenuating disc comprising:
   1. a cavity comprising an interior surface;
   2. at least one hole through said disc; and
   3. a flexible diaphragm positioned across the hollow cavity;
whereby sound pressure causes the flexible diaphragm to expand, and whereby the flexible diaphragm contacts the interior surface of the cavity at a sound pressure level at or greater than that of a peak value, thereby restricting the flexibility of the diaphragm at sound pressure levels above the peak value.

11. The non-linear sound attenuator for insertion into an ear canal of claim 10, wherein the interior surface of the cavity is of a shape to match the shape of the flexible diaphragm when the diaphragm is expanded.

12. The non-linear sound attenuator for insertion into an ear canal of claim 11, wherein the interior surface of the cavity has a concave shape.

13. The non-linear sound attenuator of claim 10, further comprising a damping member situated within the housing.

14. The non-linear sound attenuator of claim 10, wherein the at least one hole through said disc is small compared to the size of the cavity.

15. The non-linear sound attenuator of claim 14, the cavity having a diameter, wherein the diameter of the at least one hole is about 0.0026 inches and the diameter of the cavity is about 0.190 inches.

16. The non-linear sound attenuator of claim 10, wherein the attenuator provides a greater sound attenuation for external sound pressure levels above said peak value than for external sound pressure levels below the peak value.

17. The non-linear sound attenuator of claim 16, wherein said peak value is approximately 150 dB.

18. The non-linear sound attenuator of claim 16, wherein said peak value is approximately 110 dB.

19. A method for attenuating sound at a lower level where the sound pressure level external to the ear is below a peak value, and attenuating sound at a higher level where the sound pressure level external to the ear is above said peak value comprising the steps:
 a. providing a housing with a passageway for insertion into the ear;
 b. providing an attenuating disc within said housing;
 c. providing at least one hole within said disc;
 d. providing a cavity within the disc encased by an interior surface of the disc; and
 e. providing a flexible diaphragm positioned across the hollow cavity;
whereby sound pressure levels below a predetermined level do not cause the flexible diaphragm to contact the interior surface of the disc and sound pressure levels at and beyond the predetermined level cause the flexible diaphragm to contact the interior surface of the disc, thereby restricting the flexibility of the diaphragm.

20. The method of claim 19 wherein said peak value is approximately 150 dB.

21. The method of claim 19 wherein said peak value approximately 110 dB.

* * * * *